US009884194B2

(12) United States Patent
Legay et al.

(10) Patent No.: US 9,884,194 B2
(45) Date of Patent: Feb. 6, 2018

(54) USE OF AN IMPLANTABLE CARDIAC PACING, DEFIBRILATION AND/OR RESYNCHRONIZATION GENERATOR AS A VNS GENERATOR FOR VAGUS NERVE STIMULATION

(71) Applicant: SORIN CRM SAS, Clamart (FR)

(72) Inventors: Thierry Legay, Fontenay-lès-Briis (FR); Hervé Blumstein, Mévoisins (FR); Guillaume Chatalic, Clamart (FR); Christine Henry, Paris (FR)

(73) Assignee: SORIN CRM SAS, Clamart (FR)

( * ) Notice: Subject to any disclaimer, the term of this patent is extended or adjusted under 35 U.S.C. 154(b) by 204 days.

(21) Appl. No.: 14/675,291

(22) Filed: Mar. 31, 2015

(65) Prior Publication Data

US 2015/0273217 A1    Oct. 1, 2015

(30) Foreign Application Priority Data

Apr. 1, 2014   (FR) ..................... 14 52863

(51) Int. Cl.
*A61N 1/368*    (2006.01)
*A61N 1/365*    (2006.01)
(Continued)

(52) U.S. Cl.
CPC ..... *A61N 1/36585* (2013.01); *A61N 1/36053* (2013.01); *A61N 1/3684* (2013.01);
(Continued)

(58) Field of Classification Search
CPC ............ A61N 1/36053; A61N 1/36114; A61N 1/36125; A61N 1/36128; A61N 1/36139;
(Continued)

(56) References Cited

U.S. PATENT DOCUMENTS 7,200,442 B1 *   4/2007   Koh ................... A61N 1/36521
607/28
2006/0079942 A1   4/2006   Deno et al.
(Continued)

FOREIGN PATENT DOCUMENTS

EP    1 216 723    6/2002

OTHER PUBLICATIONS

Preliminary Search Report for French Patent Application No. 1452863, dated Aug. 29, 2014, 1 page.

*Primary Examiner* — Michael Carey
(74) *Attorney, Agent, or Firm* — Foley & Lardner LLP (57) ABSTRACT

On a channel of an implantable cardiac generator, a cardiac lead is replaced by a vagus nerve stimulation VNS lead. The control circuit controlling the stimulation circuit of this channel of the generator is configured to generate sequences of VNS neurostimulation bursts according to a specific profile, synchronized or not with the heart rate. The control circuit dynamically controls the initial load voltage of the reservoir capacitor so as to adjust to a constant target value the electrical charge delivered to the nerve by each stimulating pulse, from a pulse to the next one and from a burst to the next one. This improves the consistency of the physiological effects of neurostimulation despite significant variations that may occur in impedance at the electrode/vagus nerve interface.

18 Claims, 4 Drawing Sheets

(51) Int. Cl.
    *A61N 1/39*     (2006.01)
    *A61N 1/36*     (2006.01)
    *A61N 1/372*     (2006.01)

(52) U.S. Cl.
    CPC ...... *A61N 1/36114* (2013.01); *A61N 1/36125* (2013.01); *A61N 1/36139* (2013.01); *A61N 1/37264* (2013.01); *A61N 1/3962* (2013.01); *A61N 1/3987* (2013.01); *A61N 1/36128* (2013.01)

(58) Field of Classification Search
    CPC .............. A61N 1/36585; A61N 1/3684; A61N 1/37264; A61N 1/3962; A61N 1/3987
    USPC ........................ 607/2, 4, 5, 9, 11, 15, 17, 25
    See application file for complete search history.

(56) References Cited

U.S. PATENT DOCUMENTS

| | | |
|---|---|---|
| 2006/0217772 A1 | 9/2006 | Libbus et al. |
| 2009/0054939 A1* | 2/2009 | Hansen .................... A61N 1/39 607/5 |
| 2010/0114258 A1* | 5/2010 | Donofrio ................. A61N 1/37 607/63 |
| 2011/0009914 A1 | 1/2011 | Brockway et al. |
| 2011/0276103 A1 | 11/2011 | Maile et al. |
| 2012/0185010 A1 | 7/2012 | Zhou et al. |
| 2012/0290030 A1 | 11/2012 | Warman et al. |

\* cited by examiner

USE OF AN IMPLANTABLE CARDIAC
PACING, DEFIBRILATION AND/OR
RESYNCHRONIZATION GENERATOR AS A
VNS GENERATOR FOR VAGUS NERVE
STIMULATION

CROSS REFERENCE TO RELATED
APPLICATIONS

This application claims the benefit of and priority to French Patent Application No. 14/52863 (abandoned), filed Apr. 1, 2014, which is hereby incorporated by reference herein in its entirety.

BACKGROUND

The invention relates to "active implantable medical devices" as defined by Directive 90/385/EEC of 20 Jun. 1990 of the Council of the European Communities. It relates more specifically to implantable devices delivering pacing therapies to the nervous system, including stimulation of the vagus nerve. This type of stimulation will be here designated as "neurostimulation" or "VNS stimulation" (Vagus Nerve Stimulation).

The nervous system stimulation is a recognized therapy in respect of many disorders such as epilepsy, pain, heart failure, sleep apnea, obesity, etc. For the treatment of disorders such as heart failure, epilepsy or obesity, the used devices typically include a lead provided with an electrode implanted on the vagus nerve (called "VNS lead") and a generator supplying pulses VNS on this electrode.

In some therapies, the vagus nerve is stimulated synchronously with the cardiac rhythm. The device then including methods for collecting myocardium depolarization wave, typically methods for collecting an ECG by a subcutaneous electrode, or an EGM by an electrode implanted on or in the myocardium. VNS stimulation then consists in delivering a "stimulation profile" including bursts of a few VNS pulses triggered in synchronism with the cardiac rhythm. This type of VNS stimulation is particularly well suited to the treatment of heart disease, particularly in patients at risk of heart failure, when the vagus nerve stimulation acts on cardiovascular function by reducing heart rate, reducing myocardial contractility and increased diastole duration, which can help reduce the development of cardiac remodeling which may lead to an aggravated heart failure state.

In other types of therapy, the VNS stimulation profile consists of bursts or high frequency repetitive train pulses (several tens of hertz) produced during periods of "activity" of a few tens of seconds interspersed by periods of "inactivity" of a few minutes during which the stimulus is no longer issued.

In general, in the case of heart diseases, especially heart failure, the implantation of a cardiac device is frequently indicated, whether it is a pacemaker (PM, Pacemaker), an implantable Cardioverter/Defibrillator (ICD) or a resynchronizer (a device for Cardiac Resynchronization Therapy (CRT)). This stimulation, operating by delivery of pulses to the myocardium, for example by methods of an endocardial lead, will be designated hereafter as "cardiac stimulation" or "CRM (Cardiac Rhythm Management) stimulation". The patients already implanted or candidates for implantation with such an implantable cardiac device could also benefit from a VNS stimulation.

To either deliver CRM stimulation or VNS stimulation from the same implant, U.S. Pat. No. 7,660,628 proposes to provide an apparatus including a circuit for generating on the same channel either CRM pulses or VNS pulses. The pulse generator is common, but it is controlled with pulse amplitude parameters (that is to say, of voltage supplied to the electrodes) and with pulse repetition frequency which depend on the selected CRM or VNS function.

The application to the vagus nerve of pulses generated by such a device, however, is likely to produce a highly variable physiological effect, because the nervous electrode/vagus nerve interface is much more unstable than the cardiac electrode/myocardium interface. Indeed, significant changes in the biological impedance at the interface are met, which, for the same stimulation voltage, leads to widely varying currents flowing in the regions of the vagus nerve to be stimulated, with the result of physiological effects which can vary erratically due to the variable and unpredictable intensities. Specifically, the teachings of this document do not provide a device providing a satisfactory VNS stimulation, even if the cardiac stimulation generator is programmed to deliver pulses at a rate and in a profile suitable for VNS stimulation.

U.S. Pat. No. 8,478,404 describes another combination device, including a separate circuit to generate on a single channel either CRM pulses or VNS pulses. The pulse generator includes circuitry for controlled charge and discharge of a capacitor, with a switchable current source connected in series in the discharge circuit. In the case of CRM stimulation, the discharge path bypasses that current source which is neutralized, so that the capacitor discharge voltage is directly applied to the electrodes connected to the generator. In contrast, in the case of VNS stimulation, the current source inserted in the discharge path of the capacitor has the effect of regulating the current of the delivered pulse, and therefore allows accurate adjustment of the amount of charge applied to the nerve in contact with the electrodes.

It is thus possible to combine in one device the CRM stimulation and VNS stimulation functionalities. However, the device is initially specifically designed for this dual function and at the cost of increased complexity (presence of a current source, various switching circuit elements, etc.) therefore with high overall cost, both in the development stage and during manufacturing. The need therefore remains to have a simplified mixed CRM/VNS generator, including at the hardware level, with conventional circuits based on the controlled charge/discharge of a capacitor but neither implementing current sources nor additional switching elements.

Thus, a first object of the invention is to reduce the unit cost of the devices for VNS stimulation, using for this a hardware part similar to what is already included in an implantable pacemaker, by adjusting the equipment for implementation without significant additional cost.

Another aspect of the present invention results in that in some patients (a relatively large proportion, around 30% of these patients) implanted with a cardiac resynchronizer (CRT device) do not respond to CRT therapy and implantation of the device has provided no positive effect. However, these patients could be responders to VNS therapy, but in this case, it would be necessary to use another device, thereby requiring further surgery to explant the CRT device and implant a VNS device, with all the disadvantages and the costs associated with such an intervention.

Another aim of the invention is to provide a usable VNS generator for patient categories described above, in particular for patients already implanted with a pacemaker/defibrillator that could be subjected, with a benefit, to an additional VNS stimulation. For these patients, it would be preferable to have a device, including a generator, combining in one housing both (cardiac and VNS) therapies, with a significant advantage both for patient comfort and for the cost supported by the health system.

The basic idea of the invention is to use a pacemaker generator, that is to say, originally intended for stimulation of one or more cavities (ventricle or atrium) of the myocardium, and to adapt this device to make it capable of vagus nerve stimulation instead of stimulating a ventricle or an atrium.

As explained in the detailed description, this adaptation can be achieved by change of the cardiac generator control software only. Thus, the hardware of the VNS stimulation device being identical to that which already exists for a pacemaker, VNS stimulation may, by applying the invention, be implemented without significant additional cost. Notably, VNS stimulation may be implemented without the addition of any current source or additional switching elements while keeping the conventional architecture of voltage controlled charge/discharge circuits.

In particular, as will also be seen, this adaptation to transform a pacemaker into a VNS stimulator can be performed even in a patient already implanted, retaining the same generator—therefore without explantation of the device—and by connecting to one of the generator channels (e.g. the atrial channel) a VNS lead instead of a cardiac lead. Another channel connected to a cardiac lead (e.g. the ventricular channel connected to an endocardial lead) may be optionally used for the synchronization of the VNS pulses on the cardiac rhythm, if such a neurostimulation profile is selected.

This principle is not only applicable to a simple pacemaker but also to an implantable defibrillator (thus retaining the ability to deliver a antitachycardia shock therapy). It is also applicable to a resynchronizer (CRT device), by reusing one of the ventricular channels to adapt it to the purposes of VNS stimulation, another ventricular channel being retained for the collection of a synchronization signal of the VNS therapy and possibly being used for the delivery of pacing pulses in conjunction with VNS stimulation.

This same principle can be extrapolated to patients who fall under such indication, the substitution of a VNS stimulation to cardiac stimulation, all channels of the pacemaker generator (single, double or triple chambers) being reused as the same number of neurostimulation channels, by connection to one or more respective leads.

Note that if the patient is already implanted, this transformation can be performed without explantation of the generator, the intervention being restricted to the implantation of one or more VNS leads and to their connection to the generator (with or without explantation, if necessary, of the moot cardiac leads).

However, in all these cases, a pacemaker generator is not suitable for the delivery of VNS pulses. Indeed, as explained above, the application to the vagus nerve of pulses at constant voltage produce an unpredictable physiological effect due to widely varying currents circulating in the vagus nerve zones to stimulate, producing physiological effects that can erratically vary due to these variable and unpredictable intensities. Therefore, the simple substitution of a cardiac lead with a VNS lead cannot achieve the desired result, even when the cardiac stimulation generator is programmed to deliver pulses at a rate and with a profile adapted to VNS stimulation.

SUMMARY

To solve this problem, the invention proposes to adapt the generator to dynamically control the unitary electrical charge quantity delivered to the vagus nerve by the generated pulses by adjusting this charge quantity at a substantially constant value from one pulse to the next and from one burst to the next. In particular, the invention proposes to use the module for measuring the impedance that is present in most cardiac devices to measure the electrical charge quantity delivered to the vagus nerve by the stimulation electrode, and to subsequently adjust the pulse voltage so that the measured load has a constant target value.

Essentially, such a module evaluates the voltage drop across the tank capacitor from which the stimulation pulse is delivered, between the beginning and the end of the pulse. The analysis of this voltage drop is an estimate of the charge quantity delivered to the vagus nerve during the duration of the pulse, and this measure will serve as servo variable to adjust the pre-charge voltage of the capacitor (voltage at pulse start) so as to ensure the delivery of a constant pulse charge quantity, from a VNS pulse to the next one and from a VNS burst to the next one.

In other words, the invention proposes to continuously "monitor" the output impedance and to adjust at each pulse the charging voltage of the capacitor to regulate the discharge current, and thus the charge quantity applied to the vagus nerve—and this without any recourse to a current source (a source which is furthermore generally absent from conventional cardiac generators).

It is particularly advantageously emphasized that the adaptation of the generator can be achieved by a modification of the control software of the stimulation circuit, with no change of various material organs. All circuits being already present, it is only necessary to make them work differently, by implanting a dedicated software module in the generator, even though it is not possible to program a current source functionality by purely software methods.

More specifically, the invention discloses a device including, for example, the device described in U.S. Pat. No. 7,660,628 cited above. The device includes an implantable cardiac stimulation defibrillation and/or resynchronization generator, including at least two detection/stimulation terminals, with a first and a second terminal; a stimulation circuit adapted to generate electrical stimulation pulses; a control circuit adapted to control delivery on at least the first terminal of the pulses generated by the stimulation circuit and the timing of these pulses; and a circuit for collection of endocardial electrogram EGM signal and for detection of a spontaneous or stimulated cardiac depolarization wave in each cardiac cycle.

The device further comprises at least one vagus nerve stimulation (VNS) lead for implantation on or near the vagus nerve. The VNS lead is provided with connection methods suitable for a cardiac generator, and it is connected to the first terminal of the cardiac generator so as to receive the pulses produced on this terminal by the cardiac generator for applying these pulses to the vagus nerve. The control circuit of the cardiac generator is adapted to control the pacing circuit to produce pulse bursts, the pulses being VNS bursts generated continuously in succession during periods of activity separated by intermediate periods of inactivity, and/or generated in synchronism upon detection of a cardiac depolarization wave.

Typically of the invention, the control circuit is adapted to measure the impedance of the VNS lead and, in response, to dynamically control the pulse voltage generated by the stimulation circuit so as to adjust to a constant value, from a pulse to the next one and from one burst to the next one, the charge delivered by each stimulation pulse. Preferably, the connection methods adapted to a cardiac generator include an IS-1 connector mounted on the VNS lead.

In a particularly advantageous preferred embodiment, the stimulation circuit includes a capacitor and methods for charging and discharging the capacitor selectively controlled by the control circuit. The control circuit includes: methods for measuring i) the pre-charge voltage of the capacitor and ii) the voltage drop across the capacitor during the duration of the discharge; methods for calculating, from said pre-charge voltage measurements and said voltage drop, the electric charge actually delivered by the stimulation pulse produced by the discharge of the capacitor; methods for calculating the deviation between the calculated electrical charge and a reference value corresponding to said constant value of electrical charge delivered at each pulse; and methods for adjusting the pre-charge voltage of the capacitor as a function of the deviation thus calculated, in a direction reducing the gap.

The invention also provides, for example:

the use of an implantable cardiac generator as above, in combination with a VNS pacing lead adapted to be implanted on the vagus nerve or near thereto, to obtain a VNS active medical device;

a method of converting an implantable cardiac stimulation defibrillation and/or resynchronization generator, in a VNS generator according to the above technique; or a conversion software of an implantable cardiac generator in a VNS generator for implementing this method.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the device of the invention will now be described. Regarding its software aspects, the invention may be implemented by appropriate programming of the controlling software of a stimulator, for example a cardiac pacemaker, resynchronizer or defibrillator, including methods of acquisition of a signal provided by endocardial leads. The invention may notably be applied to implantable devices, such as that of the Reply (pacemakers) Paradym (ICDs and resynchronizers) family, manufactured and commercialized by Sorin CRM, Clamart, France.

These devices include programmable microprocessor circuitry to receive, format and process electrical signals collected by implantable electrodes, and deliver stimulation pulses to these electrodes. It is possible to download, by telemetry, software that is stored in memory and executed to implement the functions of the invention that are described below. The adaptation of these devices to implement additional functions, such as the inventive functions described below, is within the skill in the art and will not be described in detail.

The invention is primarily implemented by software; by appropriate algorithms executed by a microcontroller or a digital signal processor. For the sake of clarity, the various processing applied will be broken down and diagrammed by a number of different functional blocks in the form of interconnected circuits, however this representation is only illustrative, these circuits incorporating common elements and in practice corresponding to a plurality of functions performed by a single overall software.

Figure 1:
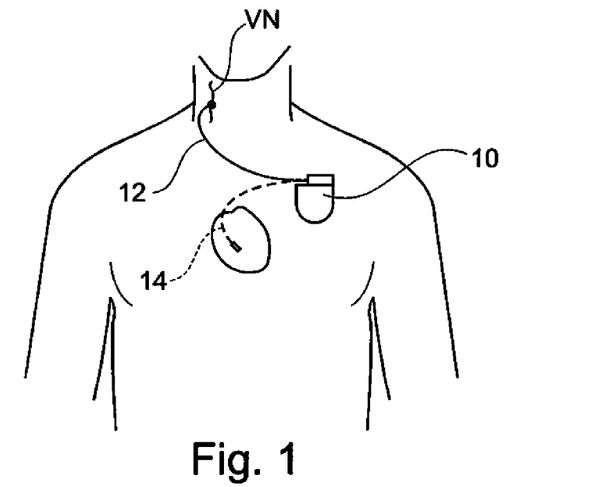
FIG. 1 is a presentation overview of the medical device of the invention, showing the generator, the vagus nerve and the VNS lead used.

In FIG. 1, the reference 10 designates the housing of an implantable generator for vagus nerve stimulation (VNS stimulation). This stimulation is delivered by a lead 12 bearing at its distal portion an electrode implanted on the vagus nerve VN and stimulating by application of VNS pulse bursts produced by the generator 10. If the VNS stimulation profile provides delivery of pulses in synchronism with the heartbeat, the generator 10 also provides a cardiac lead 14 provided at the distal end of an electrode collecting the electrical activity of the myocardium. This lead collects endocardial electrogram EGM signals that control the generator 10 so that it delivers to the vagus nerve VNS stimulation pulses at the same rate as the heart beats.

Figure 2:
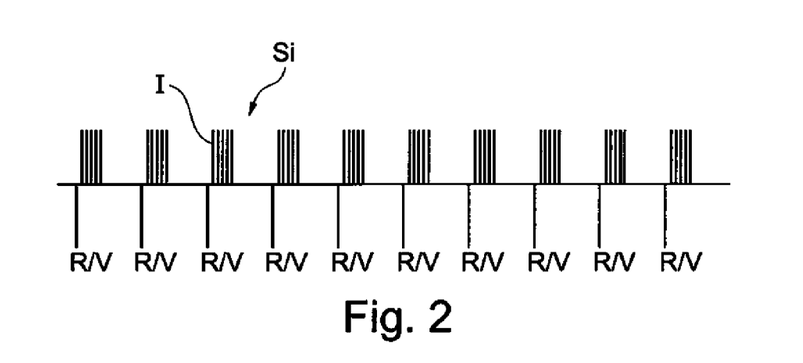
FIG. 2 is a timing diagram explaining a first neurostimulation profile, in which the VNS pulses are delivered in the form of short pulse trains synchronized to cardiac events.

In FIG. 2, a first neurostimulation profile is illustrated wherein the generator supplies VNS pulse bursts $S_i$ in synchronism with the heartbeat, the latter typically being materialized and followed by markers corresponding to the instants of occurrence of the R wave, which is representative of the peak of spontaneous depolarization of the ventricles, or of instants V of application of a ventricular pacing pulse. Other detection techniques of the heart rate can be employed alternatively or in addition to a detection of the QRS complex (R or V markers), for example techniques based on the detection of the P wave (atrial sensing) or even of the T wave (ventricular repolarization).

The bursts $S_i$ of VNS pulses are applied with or without delay after the R/V wave. Each burst $S_i$ includes of a plurality of individual pulses I in small numbers, for example two to four successive pulses. The pulses have the same amplitude and the same width, so that the pulses individually issue the same VNS stimulation energy. The interval between two successive pulses I of the same burst is preferably a constant interval. This type of neurostimulation profile is well suited to the treatment of heart disease, especially for patients at risk of heart failure.

Figure 3:
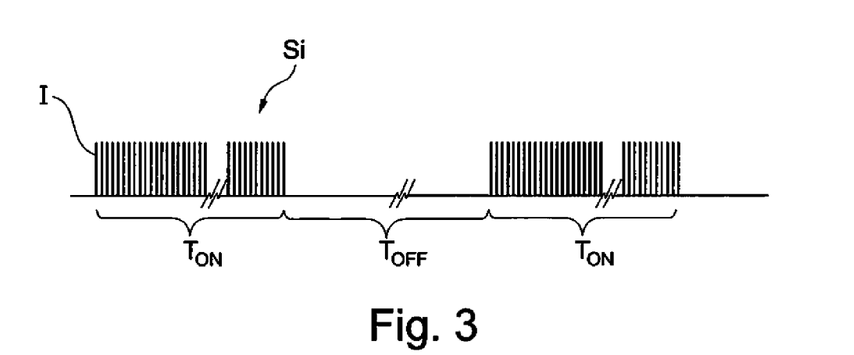
FIG. 3 is a timing diagram explaining a second neurostimulation profile, wherein the VNS pulses are delivered in the form of long pulse trains non-synchronously delivered during predetermined periods of stimulation alternating with rest intervals of also predetermined duration.

FIG. 3 illustrates another type of neurostimulation profile, not synchronized with the heartbeat, suitable, for example, for treating pathologies which are not directly related to the functioning of the heart, such as epilepsy or obesity. This profile is to deliver sustained VNS pulse bursts during "activity" periods $T_{on}$, interspersed with "inactivity" periods $T_{off}$. The repetition rate of the pulses I produced by the VNS generator is typically between 8 and 50 Hz, with bursts $S_i$ produced during periods of activity $T_{on}=30$ seconds, alternating with periods of inactivity $T_{off}=5$ minutes.

Cardiac pathologies may also be treated with such stimulation profile alternating periods of activity and periods of inactivity, since the pulses delivered during periods of activity are synchronous with the heartbeat.

The basic idea of the invention, as described in the introduction, is to produce these VNS pulse bursts not using a VNS generator (dedicated medical device) but a cardiac pacing generator (pacemaker, defibrillator and/or resynchronizer), whether it is:

a device for a first implantation; it is then possible to rationalize the manufacturing of the device, by using the same hardware, the processing of the cardiac pacing function in VNS stimulation resulting only from a software change; or a cardiac device already implanted in a patient; the procedure is then limited to the implantation and connection of a VNS lead and to the software reprogramming of the generator, without exchange or even explantation thereof.

Figure 4:
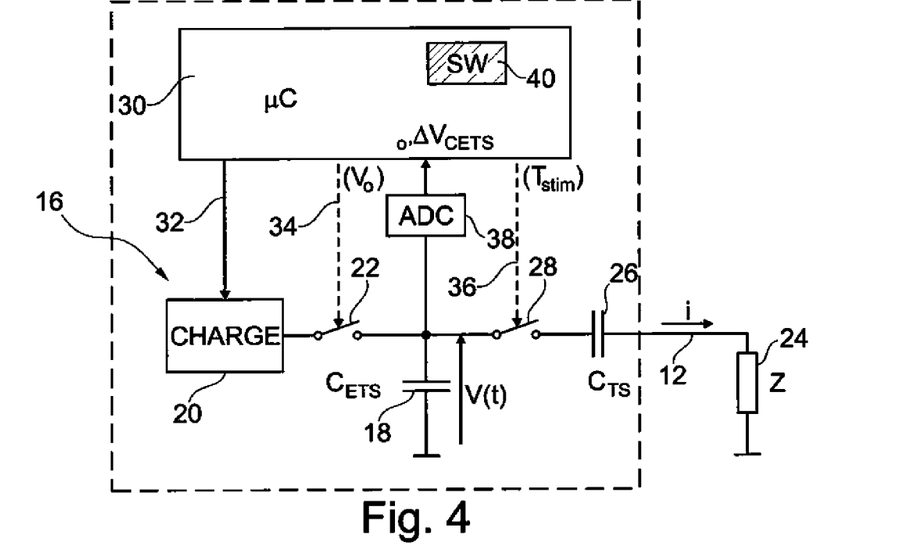
FIG. 4 is a schematic block representation of the stimulation and control circuitry of one of the channels of the generator used for the implementation of the invention.

FIG. 4 is a schematic block representation of the stimulation and control circuitry of one of the channels of the generator 10 used for the implementation of the invention. The pacing circuit 16 is a conventional pacemaker circuit, with a tank capacitor 18 of capacity CETS previously charged to a charging voltage $V_0$ by a load circuit 20, after closure of the switch 22. Once the pre-charge voltage $V_0$ is reached, the capacitor 18 is ready to be discharged into the patient's tissue, the electrode/tissue interface and the tissue being electrically modelled in 24 by a value of impedance Z at the end of the lead 12 connecting the generator 10 to the stimulation site. The discharge of the capacitor 18 occurs via a coupling capacity CTS 26 capacitor and a switch controlled to discharge the capacitor 18 during a period $T_{stim}$ corresponding to the programmed duration of the stimulation pulse.

Figure 5:
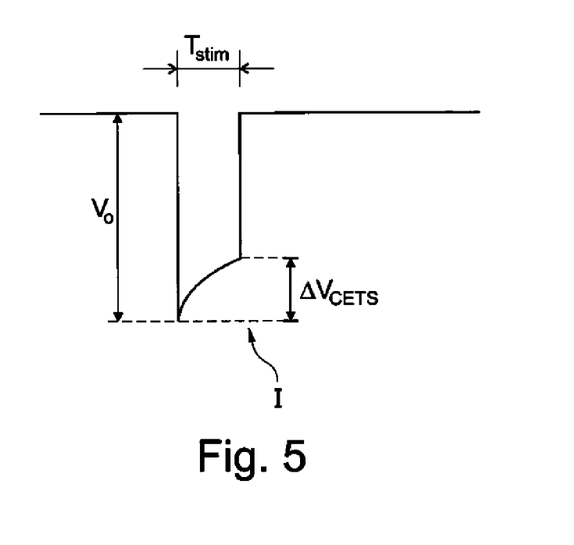
FIG. 5 shows the profile of a pacing pulse delivered by the circuits of FIG. 4, with the various parameters involved in the implementation of the invention for this pulse applied to the vagus nerve as a VNS stimulation pulse.

This pacing pulse is shown in FIG. 5 with the different parameters that characterize it, namely the pre-loading voltage $V_0$, the duration of the pulse $T_{stim}$ and the voltage drop $\Delta V_{CETS}$ observed across the capacitor 18 between the closing time and the opening time of the controlled switch 28.

The control of the various hardware components just described above is provided by a control circuit 30 which determines the pre-loading voltage $V_0$ of the load circuit 20 (arrow 32) and the sequencing of controlled switches of charge 22 and discharge 28 (arrows 34 and 36). The control circuit 30 also receives as input a signal for measuring the instantaneous voltage V(t) across the capacitor 18 via an analog/digital converter 38.

In particular, the time of closing the charging switch 22 determines the value of the pre-loading voltage $V_0$ brought to and maintained across the capacitor 18 before it is discharged. In other words, after the issuance of a pulse, the control circuit 30 closes the switch 22 to recharge the capacitor 18 and, once the measurement circuit 38 indicates that the voltage across this capacitor is $V(t)=V_0$, it opens the switch 22 to maintain to this target value the $V_0$ voltage across the capacitor 18 until the time of delivery of the pulse. The measurement circuit 38 then enables the control circuit 30 to determine the voltage drop parameter $\Delta V_{CETS}$ between the beginning and the end of the stimulation pulse.

The circuits just described above are described, for example, in EP 1216723 (Sorin CRM S.A.S. previously known as ELA Medical), which also explains the method to measure the impedance Z from measurements made from the profile of the pulse delivered to the tissues via the lead. According to the prior art, the impedance assessment procedure is carried out only from time to time, to determine the evolution over time of the electrical characteristics of the lead/myocardium interface. These characteristics can in fact change for various reasons, particularly the modification of the lead head environment (formation of contact reactive tissue) and the alteration of the conductive material forming the electrode of the lead.

The aim is to measure the impedance of the lead to see if it remains within acceptable limits and to possibly adjust the electrical parameters of delivering of the stimulation pulse, especially to avoid excessive energy consumption that could affect the lifespan of the generator.

In the case of the present invention, the impedance evaluation circuit is used for another purpose. It is to determine from the measured $V_0$ and $\Delta V_{CETS}$ parameters, and knowing $T_{stim}$, the load (amount of current) issued by the pulse I, and to readjust, from one pulse to the next one, and from one burst to the next one, the pre-loading voltage $V_0$ of the capacitor, which thus becomes a modifiable parameter at each pulse, so that the charge delivered to the tissue is an almost constant load. That is to say that, for the same pulse duration $T_{stim}$, the delivered average current is almost a constant current.

It is thus ensured that each stimulation pulse delivered to the vagus nerve will produce the same physiological effect, despite variations in the interface between the conductive material of the electrode and the vagus nerve, the impedance of which is likely to significantly change on relatively short periods (the neural interface being much more unstable than the cardiac interface).

At the beginning of the method, the control circuit 30 evaluates the charge delivered by the pulse and compares it to a target value, more precisely by comparing the measured voltage drop $\Delta V_{CETS}$ to a set defined by a voltage drop $\Delta V_0$ corresponding to the target value. The pre-loading voltage $V_0$ of the capacitor is then readjusted for the following pulses according to the measurement/setpoint difference thus determined, in a direction reducing the gap. Once the target value is reached, it is considered that the charge delivered with each pulse to the vagus nerve is the desired value, the control being then reduced to a simple tracking of stabilization around the target value.

As will be appreciated, the implementation of this adjustment method is performed in the control circuit 30, which allows the cycle-to-cycle adjustment of the pre-loading voltage $V_0$ and the timing (time, repetition frequency) of the stimulation pulse bursts. Such a circuit is generally designed around a microcontroller, in which it is sufficient to implement a software module 40 dedicated to the VNS stimulation, without modification of any hardware components (capacitor 18, charging circuit 20, charge/discharge switch 22, 28, circuit 38 for measuring the voltage across the capacitor) controlled by the control circuit 30.

FIGS. 6-9 illustrate various methods to implement the invention from pre-existing implanted or implantable cardiac devices. In these figures, the left side illustrates the cardiac device (pacemaker, defibrillator or resynchronizer) in its conventional configuration, that is to say wherein it is used in combination with leads leading to stimulation sites on the myocardium, while on the right side, the same device is shown in use according to the teachings of the invention, that is to say as VNS stimulation device connected to a lead leading to a stimulation site on the vagus nerve.

The VNS leads are, for example, those produced and sold by the company Sorin Belgium (previously known as Neurotech SA, Louvain-la-Neuve, Belgium). They can be adapted to the invention in a simple method by modifying the lead connector, replacing the proprietary connector (for coupling to a dedicated implantable neurostimulator) by a connector allowing connection to a pacemaker, typically an IS-1 standard connector.

The other change to operate is the loading into the microcontroller of the cardiac generator of the software module 40 to perform the functions described above, including the sequencing of the pulses in the form of controlled bursts and, for each pulse, the control of the pulse for it ensures the delivery to the nerve of a nearly constant electric charge.

Figure 6:
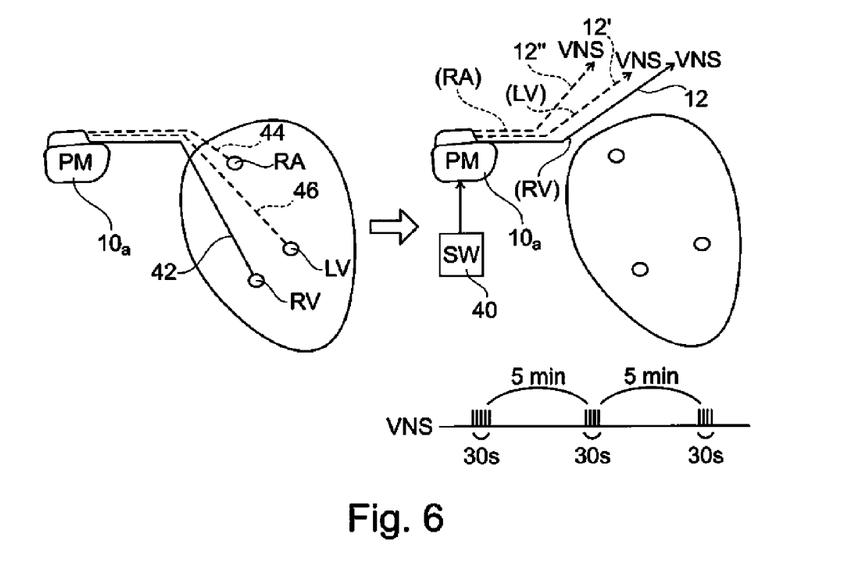
FIG. 6 shows a first method of implementation of the invention, by a simple, double or triple chamber pacemaker adaptation, for the production of a non-synchronized neurostimulation profile as that of FIG. 3.

FIG. 6 shows a first configuration wherein the VNS stimulation device is made from a single, double or triple chamber pacemaker, such as a stimulator of the Reply family from Sorin CRM. In its conventional configuration (cardiac pacing), the generator 10a includes one, two or three channels of detection/stimulation with one, two or three respective terminals, connected to a right ventricular site RV by a lead 42 and optionally to a right atrial site RA by a lead 44 and to a left ventricular site LV by a lead 46.

In the configuration according to the invention (VNS stimulation), the RV channel of the generator 10a is connected to a VNS lead 12 and, where appropriate, the RA and LV channels to other VNS leads 12' and 12". In particular if there are two VNS stimulation channels, it may be advantageous to deliver signals in opposite phase on the vagus nerve.

This VNS stimulation configuration is especially suitable for the delivery of unsynchronized pulse trains such as those which have been illustrated and described in FIG. 3, that is to say typically pulse bursts of frequency between 8 and 50 Hz, for example for periods $T_{on}$ of 30 seconds interspersed of periods $T_{off}$ of 5 minutes. Such unsynchronized neurostimulation profile on the heart rate is particularly suitable for treatment of conditions such as epilepsy or obesity.

Figure 7:
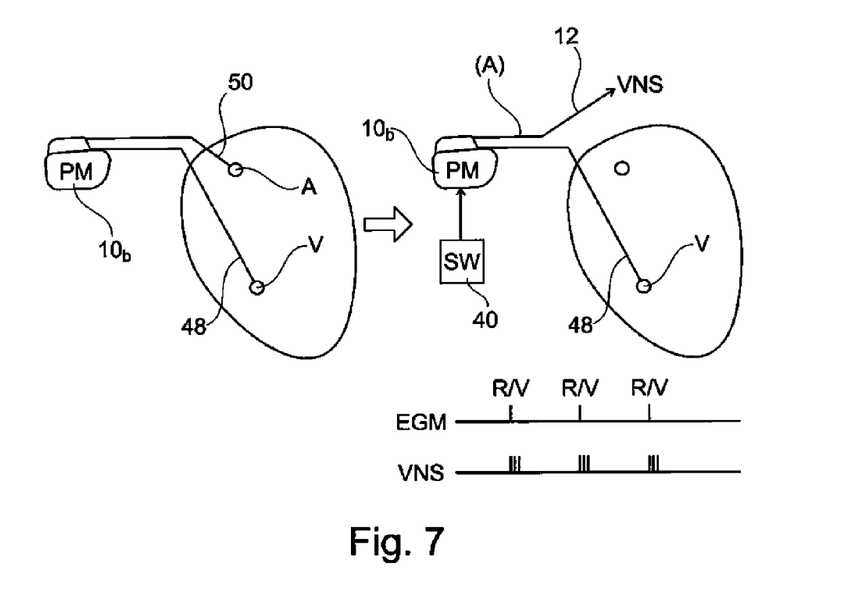
FIG. 7 illustrates a second method of implementation of the invention, by adaptation of a dual chamber pacemaker for generating a synchronous neurostimulation profile, such as that of FIG. 2.

FIG. 7 shows a second configuration wherein the VNS stimulation device is made from a dual chamber pacemaker, e.g. a pacemaker of the Reply family from Sorin CRM. In its conventional configuration (cardiac pacing), the generator 10b includes a ventricular channel connected to a site V by a lead 48 and an atrial channel connected to an atrial site A by a lead 50.

The modification according to the invention (VNS stimulation) consists in maintaining the ventricular channel and the corresponding lead 48, replacing the atrial lead 50 by a VNS lead 12. In other words, the atrial channel is transformed into VNS channel, but without change in the ventricular channel. In particular, it is possible to obtain by this ventricular channel heart rate information (R/V marker), to deliver pulses according to a synchronous neurostimulation profile such as that illustrated in FIG. 2, typically with delivery of 2 to 4 pulses to the vagus nerve to each sensed or paced cardiac cycle, the detection/stimulation being provided by the ventricular channel of the pacemaker, which has not been modified. Such neurostimulation profile synchronized on heart rate is particularly suitable for the treatment of cardiac conditions such as heart failure.

Figure 8:
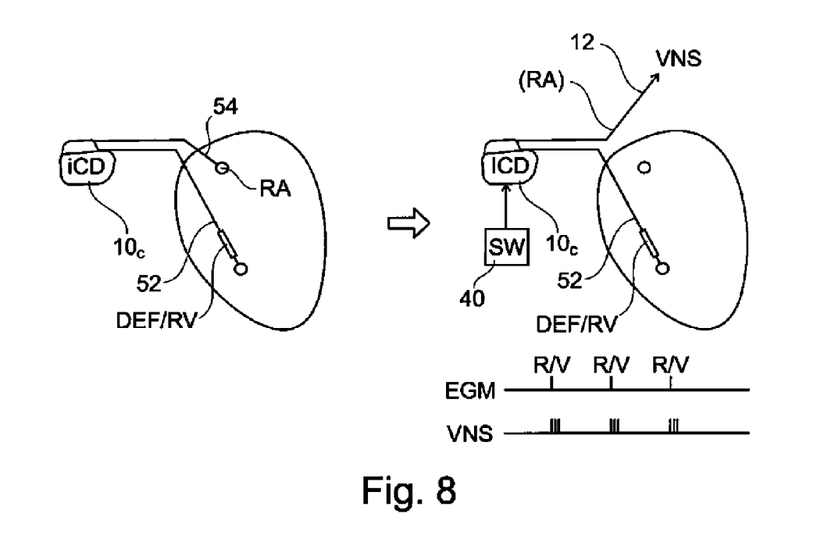
FIG. 8 shows a third method of implementation of the invention by adapting a cardiac defibrillator for producing a synchronous neurostimulation profile, such as that of FIG. 2.

FIG. 8 shows a third configuration wherein the VNS stimulation device is constructed from an implantable cardioverter/defibrillator, for example the models Paradym DR or Paradym VR from Sorin CRM. In its conventional configuration (cardiac pacing), the generator 10c is connected to a lead 52 including a defibrillation coil DEF and one or more electrodes for ventricular detection/stimulation RV, and a lead 54 for atrial detection/stimulation RA.

The modification according to the invention (VNS stimulation) consists, as in the case of FIG. 7, to replace the atrial lead 54 by a VNS lead 12 while maintaining the ventricular channel DEF/RV and the corresponding lead 52. The detection/stimulation functionalities are thus conserved (the same as in the previous embodiment) as well as that of defibrillation shock delivery, while allowing the patient to receive an additional VNS stimulation with a neurostimulation profile synchronized on heart rate.

Figure 9:
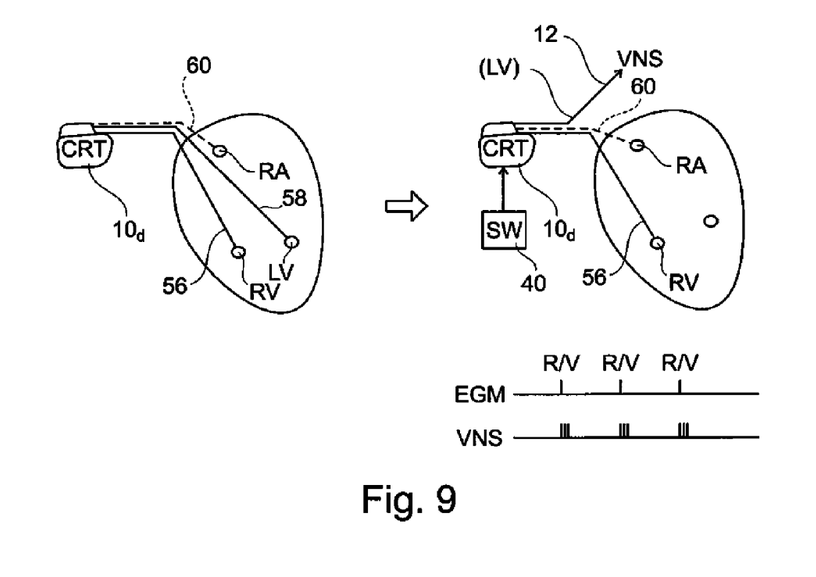
FIG. 9 shows a fourth method of implementation of the invention by adapting a resynchronizer (CRT device) for producing a synchronous neurostimulation profile, such as that of FIG. 2.

FIG. 9 illustrates a fourth possible configuration, wherein the device is a resynchronizer, e.g. Paradym CRT from Sorin CRM, that is to say a biventricular stimulation device including a generator 10d connected via a lead 56 to a right ventricular site RV and via a lead 58 to a left ventricular site LV. The generator can also be connected to a lead 60 for atrial detection/stimulation RA, present on a majority of CRT devices. Note also that the CRT device can either be a pure stimulation device (CRT-P) or be a pacing/defibrillation device (CRT-D), the ventricular lead bearing in the latter case a defibrillation coil as in the case of FIG. 8.

The modification according to the invention (VNS stimulation) is, whilst maintaining the lead 56 for right ventricular detection, to connect the left ventricular pacing channel with a VNS lead 12 for providing VNS stimulation with a neurostimulation profile synchronized on the heart rate. If the device includes an atrial lead and/or a defibrillation coil, these elements are unchanged.

This fourth configuration is advantageously applicable to patients who, after being implanted with a CRT device, finally show that they do not respond to the CRT therapy—which is usually the case for approximately 30% of these patients. The implanted device may in this case be modified to make the patient benefit from VNS stimulation, instead of or in addition to ventricular pacing (which is still possible by the lead 56 leading to right ventricular site RV). The procedure is then limited, leaving the generator 10d in place, to disconnect of it the left ventricular lead 58 (which can be left in place or explanted) and, instead, implant a lead specific for neurostimulation equipped with an appropriate connector (IS-1 connector compatible with a cardiac device generator) and finally connect the lead to the LV channel of the generator. The latter is of course reprogrammed for loading the specific software module 40 dedicated to neurostimulation.

The invention claimed is:
1. An active medical device, comprising:
an implantable cardiac generator for myocardium stimulation, defibrillation, and/or resynchronization, comprising:
  a first detection/stimulation terminal and a second detection/stimulation terminal;
  a stimulation circuit capable of generating electrical stimulation pulses;
  a control circuit capable of controlling delivery, by at least the first terminal, of the pulses generated by the stimulation circuit and a timing of these pulses; and a circuit configured to collect endocardial electrogram (EGM) signals and to detect a spontaneous or stimulated cardiac depolarization wave in each cardiac cycle; and one or more vagus nerve stimulation (VNS) leads implantable on or near a vagus nerve, each VNS lead comprising a connection mechanism configured to connect the VNS lead to the cardiac generator;

wherein:
one VNS lead is connected to the first terminal of the cardiac generator so as to receive the pulses produced on the first terminal by the cardiac generator and apply these pulses to the vagus nerve; and the control circuit of the cardiac generator is adapted to control the stimulation circuit so as to produce bursts of pulses, these bursts being VNS bursts generated continuously in succession for periods of activity separated by intermediate periods of inactivity, and/or generated synchronously on detection of a cardiac depolarization wave, characterized in that:
the control circuit is further adapted to measure an impedance of each of the one or more VNS leads during each stimulation pulse and, in response to the measured impedance of each of the one or more VNS leads, to dynamically control a pulse voltage generated by the stimulation circuit so as to adjust to a constant value, from a pulse to the next and from one burst to the next, an electrical charge delivered by each stimulation pulse.

2. The device of claim 1, wherein said connection mechanism configured to connect the VNS lead to the cardiac generator includes an IS-1 type connector mounted on the VNS lead.

3. The device of claim 1, wherein:
the stimulation circuit comprises a capacitor, a load circuit, and controlled switches configured to charge and discharge the capacitor, the controlled switches selectively controlled by the control circuit; and
the control circuit comprises:
a measurement circuit for measuring a pre-charge voltage of the capacitor and a voltage drop across the capacitor during a duration of the discharge of the capacitor; and
a memory having instructions stored thereon that, when executed, cause the active medical device to:
calculate, from said pre-charge voltage and voltage drop measurements, an electrical charge delivered by a resultant stimulation pulse produced by the discharge of the capacitor;
calculate a difference between the calculated electrical charge and a reference value corresponding to said constant value of electrical charge delivered by each pulse; and
adjust the pre-charge voltage of the capacitor according to the difference thus calculated in a direction of reduction of the difference.

4. The device of claim 1, wherein:
the cardiac generator is a generator of a double- or triple-chamber stimulator, respectively comprising two or three detection/stimulation terminals;
the control circuit of the cardiac generator is configured to control delivery, by each of the detection/stimulation terminals, of the pulses generated by the stimulation circuit and the timing of these pulses;
each of the detection/stimulation terminals is connected to a respective VNS lead so as to receive the pulses produced on each terminal by the cardiac generator and apply these pulses to the vagus nerve; and
the control circuit of the cardiac generator is adapted to control the stimulation circuit to produce the VNS bursts continuously in succession during periods of activity separated by intermediate periods of inactivity.

5. The device of claim 1, wherein:
the cardiac generator is a generator of a dual-chamber pacemaker, wherein the first terminal is an atrial terminal and the second terminal is a ventricular terminal;
the device further comprises a ventricular detection lead adapted to be implanted in a right ventricular cavity of a myocardium;
the ventricular terminal is a detection/stimulation terminal connected to the ventricular detection lead;
the circuit configured to collect EGM signals and to detect a cardiac depolarization wave is coupled to the ventricular terminal such that the ventricular detection lead is configured to collect cardiac depolarization waves; and
the control circuit of the cardiac generator is adapted to control the stimulation circuit to produce the VNS bursts in synchronism with the cardiac depolarization waves collected by the ventricular detection lead.

6. The device of claim 1, wherein:
the cardiac generator is a defibrillator generator, wherein the first terminal is an atrial terminal and the second terminal is a ventricular terminal;
the device further comprises a ventricular lead comprising a shock electrode, adapted to be implanted in a right ventricular cavity of a myocardium;
the ventricular terminal is a detection/stimulation/defibrillation terminal connected to the lead comprising the shock electrode;
the circuit configured to collect EGM signals and to detect a cardiac depolarization wave is coupled to the ventricular terminal such that the ventricular lead is configured to collect cardiac depolarization waves; and
the control circuit of the cardiac generator is adapted to control the stimulation circuit to produce the VNS bursts in synchronism with the cardiac depolarization waves collected by the ventricular lead.

7. The device of claim 1, wherein:
the cardiac generator is a resynchronization generator, wherein the first terminal is a left ventricular terminal and the second terminal is a right ventricular terminal;
the device further comprises a right ventricular sensing lead adapted to be implanted in a right ventricular cavity of a myocardium;
the right ventricular terminal is a detection/stimulation terminal connected to the right ventricular sensing lead;
the circuit configured to collect EGM signals and to detect a cardiac depolarization wave is coupled to the right ventricular terminal such that the ventricular sensing lead is configured to collect cardiac depolarization waves; and
the control circuit of the cardiac generator is adapted to control the stimulation circuit to produce the VNS bursts in synchronism with the cardiac depolarization waves collected by the right ventricular sensing lead.

8. A method of converting an implantable cardiac stimulation, defibrillation, and/or resynchronization generator to a vagus nerve stimulation (VNS) generator for vagus nerve stimulation, the cardiac generator comprising:
a first detection/stimulation terminal and a second detection/stimulation terminal;

a stimulation circuit capable of generating electrical stimulation pulses;

a control circuit capable of controlling delivery, by at least the first terminal, of the stimulation pulses generated by the stimulation circuit and a timing of these pulses;

a circuit adapted to collect endocardial electrogram (EGM) signals and adapted to detect a spontaneous or stimulated cardiac depolarization wave in each cardiac cycle, the method comprising the steps of:

configuring the control circuit of the cardiac generator to control the stimulation circuit to produce bursts of pulses, these bursts being VNS bursts generated continuously in succession during periods of activity separated by intermediate periods of inactivity, and/or generated in synchronism upon detection of a cardiac depolarization wave; and configuring the control circuit to:

measure an impedance of each of one or more VNS leads during each stimulation pulse, wherein one VNS lead is connected to the first terminal of the cardiac generator so as to receive the pulses produced on the first terminal by the cardiac generator and apply these pulses to the vagus nerve; and in response to the measured impedance of each of the one or more VNS leads, dynamically control a pulse voltage generated by the stimulation circuit to adjust to a constant value, from a pulse to the next and from one burst to the next, an electrical charge delivered by each stimulation pulse.

9. The method of claim 8, wherein:

the stimulation circuit comprises a capacitor, a load circuit, and controlled switches configured to charge and discharge the capacitor, the controlled switches selectively controlled by the control circuit; and the control circuit comprises a measurement circuit configured to measure a pre-charge voltage of the capacitor and a voltage drop across the capacitor during a duration of the discharge of the capacitor; and the method further comprises:

calculating, from said pre-charge voltage and voltage drop measurements, an electrical charge delivered by a resultant stimulation pulse produced by the discharge of the capacitor;

calculating a difference between the calculated electrical charge and a reference value corresponding to said constant value of electrical charge delivered by each pulse; and adjusting the pre-charge voltage of the capacitor according to the difference thus calculated in a direction of reduction of the difference.

10. The method of claim 8, wherein:

the cardiac generator is a generator of a double- or triple-chamber stimulator, respectively comprising two or three detection/stimulation terminals;

the control circuit of the cardiac generator is configured to control delivery, by each of the detection/stimulation terminals, of the pulses generated by the stimulation circuit and the timing of these pulses;

each of the detection/stimulation terminals is connected to a respective VNS lead so as to receive the pulses produced on each terminal by the cardiac generator and apply these pulses to the vagus nerve; and configuring the control circuit to control the stimulation circuit comprises configuring the control circuit to control the stimulation circuit to produce the VNS bursts continuously in succession during periods of activity separated by intermediate periods of inactivity.

11. The method of claim 8, wherein:

the cardiac generator is a generator of a dual-chamber pacemaker, wherein the first terminal is an atrial terminal and the second terminal is a ventricular terminal;

the device further comprises a ventricular detection lead adapted to be implanted in a right ventricular cavity of a myocardium;

the ventricular terminal is a detection/stimulation terminal connected to the ventricular detection lead;

the circuit adapted to collect EGM signals and to detect a cardiac depolarization wave is coupled to the ventricular terminal such that the ventricular detection lead is configured to collect cardiac depolarization waves; and configuring the control circuit to control the stimulation circuit comprises configuring the control circuit to control the stimulation circuit to produce the VNS bursts in synchronism with the cardiac depolarization waves collected by the ventricular detection lead.

12. The method of claim 8, wherein:

the cardiac generator is a defibrillator generator, wherein the first terminal is an atrial terminal and the second terminal is a ventricular terminal;

the device further comprises a ventricular lead comprising a shock electrode, adapted to be implanted in a right ventricular cavity of a myocardium;

the ventricular terminal is a detection/stimulation/defibrillation terminal connected to the lead comprising the shock electrode;

the circuit adapted to collect EGM signals and to detect a cardiac depolarization wave is coupled to the ventricular terminal such that the ventricular lead is configured to collect cardiac depolarization waves; and configuring the control circuit to control the stimulation circuit comprises configuring the control circuit to control the stimulation circuit to produce the VNS bursts in synchronism with the cardiac depolarization waves collected by the ventricular lead.

13. The method of claim 8, wherein:

the cardiac generator is a resynchronization generator, wherein the first terminal is a left ventricular terminal and the second terminal is a right ventricular terminal;

the device further comprises a right ventricular sensing lead adapted to be implanted in a right ventricular cavity of a myocardium;

the right ventricular terminal is a detection/stimulation terminal connected to the right ventricular sensing lead;

the circuit adapted to collect EGM signals and to detect a cardiac depolarization wave is coupled to the right ventricular terminal such that the ventricular sensing lead is configured to collect cardiac depolarization waves; and configuring the control circuit to control the stimulation circuit comprises configuring the control circuit to control the stimulation circuit to produce the VNS bursts in synchronism with the cardiac depolarization waves collected by the right ventricular sensing lead.

14. A method of converting an implantable cardiac stimulation, defibrillation, and/or resynchronization generator in a vagus nerve stimulation (VNS) generator for vagus nerve stimulation, the cardiac generator comprising:

a first detection/stimulation terminal and a second detection/stimulation terminal;

a stimulation circuit capable of generating electrical stimulation pulses to be delivered by a stimulating electrode;

a control circuit capable of controlling delivery, by at least the first terminal, of the stimulation pulses generated by the stimulation circuit and a timing of these pulses; and a circuit adapted to collect endocardial electrogram (EGM) signals and adapted to detect a spontaneous or stimulated cardiac depolarization wave in each cardiac cycle, the method comprising:

controlling, by the control circuit, the stimulation circuit to generate sequences of VNS neurostimulation bursts;

wherein the control circuit controls a stimulation voltage of the stimulation circuit to dynamically adjust the electrical charge delivered to the nerve by each stimulating pulse to a constant value from a first pulse to the next pulse and from a first burst to a next burst, to improve the consistency of the neurostimulation despite variations in impedance at an interface between the nerve and the stimulating electrode.

15. The method of claim 14, wherein:

the stimulation circuit comprises a capacitor and is configured to charge and discharge the capacitor using controlled switches;

wherein the stimulation voltage is a pre-charge voltage across the capacitor; and wherein controlling the stimulation voltage comprises:

measuring the pre-charge voltage of the capacitor and a voltage drop across the capacitor during a duration of the discharge;

calculating, from said pre-charge voltage and voltage drop measurements, an electrical charge delivered by a resultant stimulation pulse produced by the discharge of the capacitor;

calculating a difference between the calculated electrical charge and a reference value corresponding to said constant value of electrical charge delivered by each pulse; and adjusting the pre-charge voltage of the capacitor according to the difference thus calculated in a direction of reduction of the difference.

16. The method of claim 15, wherein controlling the stimulation circuit to generate sequences of VNS neurostimulation bursts comprising controlling, by the control circuit, the stimulation circuit so as to produce bursts of pulses, these bursts being VNS bursts generated continuously in succession for periods of activity separated by intermediate periods of inactivity, and/or generated synchronously on detection of a cardiac depolarization wave.

17. The method of claim 16, wherein controlling the stimulation circuit to generate sequences of VNS neurostimulation bursts further comprises controlling, by the control circuit, the stimulation circuit to produce the VNS bursts continuously in succession during periods of activity separated by intermediate periods of inactivity.

18. The method of claim 16, wherein controlling the stimulation circuit to generate sequences of VNS neurostimulation bursts further comprises controlling, by the control circuit, the stimulation circuit to produce the VNS bursts in synchronism with the cardiac depolarization waves collected by a ventricular lead.

* * * * *